(12) United States Patent
Brizius

(10) Patent No.: US 9,150,734 B2
(45) Date of Patent: Oct. 6, 2015

(54) ZWITTERIONIC LIGNIN DERIVATIVES FOR MARINE ANTIFOULING COATINGS

(75) Inventor: Glen Leon Brizius, Augusta, GA (US)

(73) Assignee: Empire Technology Development LLC, Wilmington, DE (US)

( * ) Notice: Subject to any disclaimer, the term of this patent is extended or adjusted under 35 U.S.C. 154(b) by 354 days.

(21) Appl. No.: 13/522,429

(22) PCT Filed: Mar. 7, 2012

(86) PCT No.: PCT/US2012/028062
§ 371 (c)(1),
(2), (4) Date: Jul. 16, 2012

(87) PCT Pub. No.: WO2013/133823
PCT Pub. Date: Sep. 12, 2013

(65) Prior Publication Data
US 2013/0236630 A1    Sep. 12, 2013

(51) Int. Cl.
| | | |
|---|---|---|
| C07G 1/00 | (2011.01) | |
| C08H 7/00 | (2011.01) | |
| C08L 97/00 | (2006.01) | |
| C09D 5/16 | (2006.01) | |
| C09D 101/02 | (2006.01) | |
| C09D 103/02 | (2006.01) | |
| C09D 105/14 | (2006.01) | |
| C09D 197/00 | (2006.01) | |
| C09D 197/02 | (2006.01) | |
| A01N 25/10 | (2006.01) | |
| A01N 33/12 | (2006.01) | |

(52) U.S. Cl.
CPC .............. *C09D 5/1656* (2013.01); *A01N 25/10* (2013.01); *A01N 33/12* (2013.01); *C09D 101/02* (2013.01); *C09D 103/02* (2013.01); *C09D 105/14* (2013.01); *C09D 197/005* (2013.01); *C09D 197/02* (2013.01)

(58) Field of Classification Search
CPC .............. C08H 8/00; C08H 6/00; C07G 1/00; C08L 97/005; C08L 97/02; C08L 1/08; C08L 1/286; C08L 1/288; C08L 5/14; C08L 3/02
See application file for complete search history.

(56) References Cited

U.S. PATENT DOCUMENTS

| | | | | |
|---|---|---|---|---|
| 1,470,465 | A | | 10/1923 | Marquette |
| 3,398,019 | A | | 8/1968 | Langguth et al. |
| 3,676,423 | A | * | 7/1972 | Elizer ............................ 536/43 |
| 3,854,867 | A | * | 12/1974 | Ward et al. ...................... 8/116.1 |
| 4,577,013 | A | * | 3/1986 | Merz et al. ....................... 536/43 |
| 4,603,653 | A | | 8/1986 | Bews |
| 4,881,976 | A | | 11/1989 | Gradeff |
| 4,987,036 | A | | 1/1991 | Miller |
| 5,312,863 | A | * | 5/1994 | Van Rheenen et al. ....... 524/555 |
| 5,501,773 | A | * | 3/1996 | Elliott et al. .................... 162/163 |
| 5,567,277 | A | * | 10/1996 | Elliott et al. .................... 162/163 |
| 5,919,689 | A | | 7/1999 | Selvig et al. |
| 6,602,994 | B1 | * | 8/2003 | Cash et al. ........................ 536/30 |
| 8,349,966 | B2 | * | 1/2013 | Jiang et al. .................. 525/329.4 |
| 8,658,192 | B2 | * | 2/2014 | Jiang et al. ..................... 424/405 |
| 8,747,709 | B2 | * | 6/2014 | Brizius .......................... 252/601 |
| 2003/0013871 | A1 | * | 1/2003 | Mallon et al. ..................... 536/84 |
| 2005/0192434 | A1 | * | 9/2005 | Buchanan et al. ................ 536/32 |
| 2005/0215764 | A1 | * | 9/2005 | Tuszynski et al. .............. 530/358 |
| 2006/0276569 | A1 | * | 12/2006 | Richardson et al. ............ 524/47 |
| 2007/0036832 | A1 | * | 2/2007 | Williams et al. .............. 424/405 |
| 2008/0213199 | A1 | * | 9/2008 | Philippe .......................... 424/59 |
| 2009/0149673 | A1 | | 6/2009 | Zhang et al. |
| 2009/0155335 | A1 | | 6/2009 | O'Shaughnessey et al. |
| 2010/0034858 | A1 | * | 2/2010 | Champ et al. .................. 424/409 |
| 2010/0075878 | A1 | * | 3/2010 | Gizaw et al. ................... 510/119 |
| 2010/0145286 | A1 | | 6/2010 | Zhang et al. |
| 2010/0152708 | A1 | | 6/2010 | Li et al. |
| 2010/0210604 | A1 | * | 8/2010 | Meythaler ...................... 514/160 |
| 2011/0098464 | A1 | * | 4/2011 | Buchanan et al. ................ 536/65 |
| 2013/0203982 | A1 | * | 8/2013 | Buchanan et al. ................ 536/68 |
| 2013/0236630 | A1 | * | 9/2013 | Brizius ......................... 427/2.12 |
| 2013/0292615 | A1 | * | 11/2013 | Brizius .......................... 252/601 |
| 2013/0340923 | A1 | * | 12/2013 | Brizius et al. .................. 156/182 |
| 2014/0235132 | A1 | * | 8/2014 | Brizius .......................... 442/414 |

FOREIGN PATENT DOCUMENTS

| | | | |
|---|---|---|---|
| AU | 2009322136 | A1 | 6/2010 |
| CA | 2745204 | A1 | 6/2010 |
| CA | 2745440 | A1 | 6/2010 |
| CN | 102307955 | A | 1/2012 |
| EP | 2352796 | A1 | 8/2011 |
| EP | 2352797 | A2 | 9/2011 |

(Continued)

OTHER PUBLICATIONS

Zhang et al. (Journal of Applied Polymer Science, vol. 83, 2755-2761, 2002).*
International Search Report and Written Opinion for PCT/US2012/030575 dated Jun. 12, 2012.
AMBIO—Advanced Nanostructured S Control of Biofouling, http://www.birmingham.ac.uk/generic/ambio/index.aspx [Printed From Internet Jul. 1, 2012].
Barnes, et al., Toxic properties of some dialkyl and trialkyl tin salts, *Br J Ind Med.* (Jan. 1958), 15(1):15-22.
Beveridge et al., The effect of benzalkonium chloride concentration on nine species of marine diatom, *Environmental Pollution* (Oct. 1, 1998), 103(1):31-36.
Biocides, http://www.lenntech.com/biocides.htm#Quaternary%20ammonium@20salts [Printed From Internet Jul. 1, 2012].

(Continued)

*Primary Examiner* — Liam J Heincer
(74) *Attorney, Agent, or Firm* — Pepper Hamilton LLP

(57) ABSTRACT

Disclosed are antifouling compositions that can include a biopolymeric matrix which is substantially zwitterionic. The compositions may include a biopolymer matrix having positively charged functional groups, negatively charged functional groups, zwitterionic functional groups, or a combination thereof, such that the composition is substantially zwitterionic. The compositions can be used as additives and as compositions further containing a base material such as paint or lacquer. Methods of making and using such compounds and compositions are also disclosed.

22 Claims, No Drawings

(56) References Cited

FOREIGN PATENT DOCUMENTS

| | | |
|---|---|---|
| GB | 1470465 A | 4/1977 |
| KR | 20110106866 A | 9/2011 |
| SG | 171882 A1 | 7/2011 |
| WO | WO2009/075788 A1 | 6/2009 |
| WO | WO2009/085096 A2 | 7/2009 |
| WO | WO2010/065958 A1 | 6/2010 |
| WO | WO2010/065960 A2 | 6/2010 |

OTHER PUBLICATIONS

Biofuels Basics, http://www.nrel.gov/learning/re_biofuels.html [Printed From Internet Apr. 30, 2012].

Chambers et al., Modern Approaches to Marine Antifouling Coatings, *Surface & Coating Technology* (2006), 201:3642-3652.

Champ et al., A review of organotin regulatory strategies, pending actions, related costs and benefits, *Sci Total Environ.* (Aug. 21, 2000), 258(1-2):21-71.

Chen et al., An New Avenue to Nonfouling Materials, *Advanced Materials* (Dec. 20, 2007), 20(2):335-338.

Chen et al., Quaternary Ammonium Functionalized Poly(propylene imine) Dendrimers as Effective Antimicrobials: Structure-Activity Studies, *Biomacromolecules* (Aug. 1, 2000), 1(3):473-480.

Cheng et al., Zwitterionic carboxybetaine polymer surfaces and their resistance to long-term biofilm formation, *Biomaterials* (Oct. 2009), 30(28):5234-5240.

Costerton, Introduction to Biofilm, *Int J Antimicrob Agents* (May 1999), 11(3-4):217-221 (Abstract).

Crude Oil and Commodity Prices, http://www.oil-price.net/ [Printed From Internet Apr. 30, 2012].

Deepwater Horizon oil spill, http://en.wikipedia.org/wiki/Deepwater_Horizon_oil_spil [Printed From Internet Apr. 30, 2012].

Donlan et al., Biofilms: microbial life on surfaces, *Emerg Infect Dis.* (Sep. 2002), 8(9):881-90.

Evans et al., Tributyltin pollution: a diminishing problem following legislation limiting the use of TBT-based anti-fouling paints, *Marine Pollution Bulletin* (Jan. 1995), 30:14-21.

Freger et al., TFC polyamide membranes modified by grafting of hydrophilic polymers: an FT-IR/AFM.TEM study, *Journal of Membrane Science* (Nov. 1, 2002), 209(1):283-292.

Gardel et al., Cell-substrate interactions, *J. Phys.: Condens. Matter* (2010), 22:1-4.

Gawel, et al., Zwitterionically modified hydroxypropylcellulose for biomedical applications, *European Polymer Journal* (Apr. 24, 2010), 46:1475-1479.

Graf, Benzalkonium chloride as a preservative in nasal solutions: re-examining the data, *Respir.* (Sep. 2001), 95(5):728-733.

H NMR Spectroscopy for Lignin Analysis, http://www.ipst.gatech.edu/faculty/ragauskas_art/technical_reviews/H%20NMR%20of%20Lignin.pdf [Printed From Internet Jul. 1, 2012].

Hallas et al., Factors Affecting the Toxic Effect of Tin on Estuarine Microorganisms, *Applied and Environmental Microbiology* (Jul. 1982), 44(1):193-197.

Hazziza-Laskar et al., Biocidal polymers active by contact. I. Synthesis of polybutadiene with pendant quaternary ammonium groups, *Journal of Applied Polymer Science* (Oct. 1993), 50(4):651-652.

Herzberg et al., Impact of microfiltration treatment of secondary wastewater effluent on biofouling of reverse osmosis membranes, *Water Research* (Jan. 2010), 44(1):167-176 (Abstract).

Herzberg et al., Surface Properties and Reduced Biofouling of Graft-Copolymers That Possess Oppositely Charged Groups, *Biomacromolecules*, (Mar. 1, 2011), 12(4):1169-1177 (Abstract).

Holladay et al., Top Value Added Chemicals from Biomass vol. II—Results of Screening for Potential Candidates from Biorefinery Lignin, DOE (PNNL, NREL), University of Tennessee, 2007.

Hugues et al., Complexation of an acrylic resin by tertiary amines: synthesis and characterisation of new binders for antifouling paints, *European Polymer Journal* (2003), 319-326.

Jia et al., Synthesis and antibacterial activities of quaternary ammonium salt of chitosan, *Carbohydrate Research* (Jun. 22, 2001), 333(1):1-6.

Kanazawa et al., Novel polycationic biocides: Synthesis and antibacterial activity of polymeric phosphonium salts, *Journal of Polymer Science Part A: Polymer Chemistry* (Feb. 1993), 31(2):335-343.

Kenawy et al., Biologically active polymers. V. Synthesis and anti-microbial activity of modified poly(glycidyl methacrylate-CO-2-hydroxyethyl methacrylate) derivatives with quaternary ammonium and phosphonium salts, *Journal of Polymer Science Part A: Polymer Chemistry* (Jul. 15, 2002), 40(14):2384-2393.

Kilduff et al., Photochemical modification of poly(ether sulfone) and sulfonated poly(sulfone) nanofiltration membranes for control of fouling by natural organic matter, *Desalination* (2000), 132:133-142.

Labare et al., Magnification of Tributyl Tin Toxicity to Oyster Larvae by Bioconcentration in Biofilms of *Shewanella colwelliam*, *Applied and Environmental Microbiology* (Oct. 1997), 63(10):4107-4110.

Ladd et al., Zwitterionic polymers exhibiting high resistance to non-specific protein adsorption from human serum and plasma, *Biomacromolecules* (May 2008), 9(5):1357-1361.

Li et al., Ultralow Fouling Zwitterionic Polymers Grafted from Surfaces Covered with an Initiator via an Adhesive Mussel Mimetic Linkage, *J. Phys. Chem. B* (Nov. 5, 2008), 112(48):15269-15274.

Majumdar et al., Combinatorial materials research applied to the development of new surface coatings IX: an investigation of novel antifouling/fouling-release coatings containing quaternary ammonium salt groups, Biofouling, (2008), 24(3):185-200.

Marple et al., Safety review of benzalkonium chloride used as a preservative in intranasal solutions: an overview of conflicting data and opinions, *Otolaryngol. Head Neck Surg.*(Jan. 2004), 130(1):131-41.

Naldrett, The importance of sulphur cross-links and hydrophobic interactions in the polymerisation of barnacle cement, *J Mar Biol Ass UK* (May 11, 2009), 73:689-702 (Abstract).

Nanotechnology News Channels http://www.azonano.com/nanotechnology-news-index.aspx [Printed from Internet Jul. 1, 2012].

Norde, Surface-Tethered Polymers to Influence Protein Adsorption and Microbial Adhesion, *ChemInform* (Aug. 28, 2007), 38(35).

Ostuni et al., A Survey of Structure—Property Relationships of Surfaces that Resist the Adsorption of Protein, *Langmuir* (2001), 17:5605-5620.

Rossmoore, Nitrogen Compounds, Fifth Edition (2001), Disinfection, Sterilization, and Preservation, Lippincott Williams & Wilkins, Philadelphia, PA.

Russell, Principles of Antimicrobial Activity and Resistance, Fifth Edition (2001), Disinfection, Sterilization, and Preservation, Lippincott Williams & Wilkins, Philadelphia, PA.

Soft Wood Lignin Wood Fragment, http://sci.waikato.ac.nz/farm/images/lignin%20structure%20RF.jpg [Printed From Internet Jul. 16, 2012].

Stoner et al., Studies on the toxicity of alkyl tin compounds, *Br J Pharmacol Chemother*. (Mar. 1955), 10(1):16-25.

Strand et al., Accumulation and trophic transfer of organotins in a marine food web from the Danish coastal waters, *Sci Total Environ.* (Nov. 1, 2005), 350(1-3):72-85 (Abstract).

Stringer et al., Pollution with organic tin compounds, organochlorines, hydrocarbons and metals in sediment samples from Guanabara Bay, Rio de Janeiro, Brazil, Greenpeace Research Laboratories, Department of Biological Sciences, University of Exeter, Exeter, UK (Dec. 2000).

Stupak et al., Non-toxic alternative compounds for marine antifouling paints, *International Biodeterioration & Biodegradation* (Jul. 2003), 52(1):49-52.

Terlizzi et al., Environmental impact of antifouling technologies: state of the art and perspectives, *Aquatic Conservation: Marine and Freshwater Ecosystems*, (Jul. 24, 2001), 11(4):311-317 (Abstract).

The Effects of Fouling, Marine Fouling and Its Prevention, Contribution No. 580 from the Woods Hole Oceanographic Institute, U.S. Naval Institute, Annapolis, MD (1952).

Thrash et al., Physical Factors Influencing the Activity of Antimicrobial Agents, Fifth Edition (2001), Disinfection, Sterilization, and Preservation, Lippincott Williams & Wilkins, Philadelphia, PA.

(56) References Cited

OTHER PUBLICATIONS

Townsin, The Ship Hull Fouling Penalty, *Biofouling: The Journal of Bioadhesion and Biofilin Research* (Sep. 9, 2010), 19(S1):9-15 (Abstract).

Tsukamoto et al., Pseudoceratidine: A new antifouling spermidine derivative from the marine sponge *Pseudoceratina purpurea*, *Tetrahedron Letters*, (Feb. 26, 1996), 37(9):1439-1440.

Tsuneda et al., Extracellular polymeric substances responsible for bacterial adhesion onto solid surface, *FEMS Microbiol. Letters* (Jun. 27, 2003), 223(2):287-292.

Weavers et al., Kinetics of the Inactivation of Microorganisms, Fifth Edition (2001), Disinfection, Sterilization, and Preservation, Lippincott Williams & Wilkins, Philadelphia, PA.

Zhang et al., Nonfouling Behavior of Polycarboxybetaine-Grafted Surfaces: Structural and Environmental Effects, *Biomacromolecules* (Sep. 12, 2008), 9(10):2686-2962.

Biocide-Free Antifouling Coatings Thanks to Nanostructured Surfaces, accessed at http://web.archive.org/web/20080819060408/ http://www.azonano.com/News.asp?NewsID=1282 accessed on Nov. 4, 2014, pp. 1-3.

International Search Report and Written Opinion for PCT/US2012/ 028062 dated Jun. 12, 2012.

Jiang et al., Ultralow-Fouling, Functionalizable, and Hydrolyzable Zwitterionic Materials and Their Derivatives for Biological Applications, *Adv. Mater.* (2010), 22:920-932.

Norde, Surface-Tethered Polymers to Influence Protein Adsorption and Microbial Adhesion, *ChemInform* (Aug. 8, 2007), 38(35): 38: no. doi: 10.1002/chin.200735274.

* cited by examiner

ZWITTERIONIC LIGNIN DERIVATIVES FOR MARINE ANTIFOULING COATINGS

CLAIM OF PRIORITY

This application is a U.S. national stage filing under 35 U.S.C. §371 of International Application No. PCT/US2012/028062 filed Mar. 7, 2012 entitled "Zwitterionic lignin derivatives for marine antifouling coatings" and is hereby incorporated by reference in its entirety.

FIELD

This disclosure relates to additives and compositions having antifouling properties. More specifically, this disclosure relates to such additives and compositions which are zwitterionic. More specifically, this disclosure relates to zwitterionic lignin based additives and coatings. This disclosure also relates to methods of making such additives and compositions as well as their use.

BACKGROUND

The phenomenon of biofouling is caused by the attachment of microorganisms such as bacteria to a wetted surface, which is followed by the attachment and growth of colonies of larger organisms on the surface such as plants algae or animals. Wetted surfaces are those exposed to water, moisture, humidity, water vapor, steam, condensation or ice.

Biofouling is a multistep process. Exposure of a surface or structure to water results in the adsorption of a film of dissolved organic material and colonies of bacteria appear and form a biofilm. In attaching to the surface, the bacteria release substances that provide mechanical stability through electrostatic forces such as hydrogen bonds and van der Walls interactions. As the attached bacterial cells begin to multiply, the biofilm thickens. This process is generally known as microfouling and enables the process of macrofouling. The formation of biofilms plays an important role in the next phase of biofouling known as macrofouling. Macrofouling is the attachment of larger organisms such as plants algae or animals. These larger organisms colonize biofilm coated surfaces and secrete a compound thought to be a hydrophobic glycoprotein biological adhesive which allows these organisms to become nearly permanently attached to a surface.

Biofouling represents a significant problem for any wetted surface or structure and may result in interference with the normal use and condition of the surface or structure. Such interference can lead premature break down of wetted structures and surfaces and can have significant economic implications to a number of industries.

In addition to interfering with the normal use and condition of wetted structures and surfaces, biofouling can in some cases also represent health and safety hazards due to the accumulation of microorganisms on a particular surface or structure.

Biofouling has a particularly significant impact on marine vessels. The outer hulls of marine vessels are an attractive habitat for algae and small life forms such as barnacles, which latch on and begin to form a layer of biological material attached to the ship. This phenomenon is known as "biofouling". Biofouling is caused by the attachment of bacteria, which is followed by the attachment and growth of colonies of larger organisms on the surface.

Biofouling in a marine environment is also a multistep process. Within just minutes of placing a clean surface into seawater it adsorbs a film of dissolved organic material and colonies of bacteria appear within a few hours and form a biofilm. In attaching to the hull, the bacteria release substances that provide mechanical stability through electrostatic forces such as hydrogen bonds and van der Walls interactions. As the attached bacterial cells begin to multiply, the biofilm thickens and can reach as much as 500 microns in thickness. This process is generally known as microfouling and enables the process of macrofouling. The formation of biofilms plays an important role in the next phase of biofouling known as macrofouling. Macrofouling is the attachment of larger organisms such as mussels and barnacles. These larger organisms colonize biofilm coated surfaces and secrete a compound thought to be a hydrophobic glycoprotein biological adhesive which allows these organisms to become nearly permanently attached to a surface.

Once on a vessel's hull, biofouling results in an increase in overall surface roughness, which leads to an increase in hydrodynamic drag. The associated costs include increased fuel consumption, labour costs of cleaning a vessels' hull, as well as removing and replacing damaged paint, in addition to costs associated with the downtime required for such services. Studies have found that biofouling may result in a 10% increase in a vessel's drag, which in turn results in a 40% increase in fuel consumption. Existing antifouling solutions include tin and copper compounds added to a vessel's paint coating. Although initially effective, these compounds are inadequate as they leach out of the cured paint coatings of vessels resulting in limited prevention, inhibition, delay, alleviation or reduction of biofouling and have been shown to be harmful to aquatic life. Removal of this biofouling material often requires mechanical efforts as well as refinishing (e.g. painting). Such efforts require docking the vessel and in some cases dry docking the vessel. All of this results in costly downtime of the vessel.

Accordingly, more and better ways of hindering or delaying the biofouling process on wetted surfaces are desirable.

SUMMARY

Various embodiments are directed towards, among other things, anti-fouling compositions, methods of synthesizing zwitterionic biopolymer compounds, and methods of protecting surfaces from the formation of a biofilm.

In one embodiment, anti-fouling compositions can comprise at least one biopolymer matrix. The biopolymer matrix can comprise a) one or more positively charged functional groups; b) one or more negatively charged functional groups; c) one or more zwitterionic functional groups; or d) combinations thereof. The biopolymer matrix and/or the composition can be substantially or fully zwitterionic.

In another embodiment, methods of synthesizing a zwitterionic biopolymer compound can comprise contacting at least one zwitterionic functional group with a biopolymer matrix. The zwitterionic functional group can comprise a formula: (⊕NR1R2R3)—(CR5R6⊖)n—(R7)(⊖NR1R2R3)—(CR5R6)n—(R7⊖). Each $R^1$, $R^2$, and $R^3$ can independently be C1-20 alkyl, C6-20 aryl, C3-20 cycloalkane, C1-20 alkyl acetamide of formula CnH(2n+1)—C(O)—N(CH2)2, C1-20 alkyloxybenzene, methoxy benzene, (2-ethoxy-ethoxy)-4-(1,1,3,3-tetramethyl-butyl)-benzene, N-phenyl-acetamide or an oligomer of ethylene glycol. Any two of R1, R2, and R3 may be joined together with the nitrogen to which they are attached to form a C5-7 heterocycle. Each R5 and R6 can independently be H, OH, or C1-20 alkyl. At least one R5 or R6 can be selected from —OH, C—O—C(O)—NH2 or —OC(O)OH. R7 can be —COO— or —SO2O—. The value n can be an integer from 1 to 20.

In yet another embodiment, methods of synthesizing a zwitterionic biopolymer compound can comprise: providing at least one positively charged chloroformate; providing at least one negatively charged chloroformate; and contacting the at least one positively charged chloroformate and the at least one negatively charged chloroformate with a biopolymer matrix to form a biopolymer compound comprising at least one positively charge functional group and at least one negatively charged functional group.

In an additional embodiment, methods of protecting a surface from the formation of a biofilm can comprise: providing a zwitterionic biopolymer matrix having at least one functional group selected from both positively charged and negatively charged functional groups, zwitterionic functional groups, polyethylene glycol functional groups or a combination thereof; combining the zwitterionic biopolymer matrix with a base selected from paint, coating, varnish, stain, or a combination thereof; coating the surface with the mixture; and allowing the mixture to cure, whereby the cured mixture will reduce the formation of a biofilm on the surface.

DETAILED DESCRIPTION

Application of the zwitterionic antifouling compositions described herein to the surface of a ship or other surface is useful to prevent, inhibit, alleviate, reduce, and/or delay the fouling process. The term "ship" is used in this description to encompass any waterborne structure, whether buoyant or submersible, mobile or stationary, in a body of water which may be marine, fresh, brackish, or any other water type. Thus, although the term "ship" is used herein, it is meant to include, by way of example and not limitation, waterborne structures such as vessels, ships, boats, tankers, barges, submersibles, and other watercrafts, as well as stationary items such as buoys, docks, pilings, etc.

Applicants have developed inexpensive polymeric materials which are substantially zwitterionic and provide antibacterial and/or antifouling properties. In particular, readily available biopolymers, including traditional waste material, such as lignin, may form a cheap polymeric base to such antifouling compositions. As described in more detail below, such zwitterionic antifouling compositions may take several different forms: a) a single polymer containing both separate positive functional groups and negative groups; b) a composition containing at least two polymers, one having net positive functional groups and the other having net negative functional groups; c) a polymer having zwitterionic functional groups, i.e. wherein a single functional group contains both positive and negative charges; or d) a combination of these. Additionally, compositions comprising such combinations may have a polymer containing either a positive or negative charge, along with either a) the single polymer containing both positive and negative groups or b) a polymer having zwitterionic functional groups, without having a polymer containing the opposite charge. In this manner, the substantially zwitterionic nature of the composition as a whole can be maintained.

Substantially zwitterionic, as used herein, means having both positive and negative charges. The ratio of positive to negative charges need not be 1:1. For example, for purposes of this application, zwitterionic includes compounds and compositions having at least one positive charge and at least one negative charge. Examples of mixed charges can exist in a ratio of about 1:9 to about 9:1, or ranges higher or lower than these values.

In some embodiments, the zwitterionic antifouling compositions described herein increase the hydrophilic character of the surface to which they are applied. In general, the greater the hydrophilic character of the surface the less susceptible it is to biofouling. Coating a surface with hydrophilic monomers can inhibit adsorption of various bacteria. Zwitterionic materials such as poly(carboxybetaine) and poly(sulfobetaine) can be effective in inhibiting protein adsorption, bacterial adhesion and biofilm formation. This effect appears to be due to electrostatically induced hydration of surfaces coated with these zwitterionic materials. In some embodiments, the zwitterionic anti-fouling compositions disclosed herein may inhibit or prevent adsorption of bacteria to a particular surface coated with anti-fouling composition.

Certain embodiments are directed to an anti-fouling composition comprising at least one biopolymer matrix comprising one or more positively charged functional groups; one or more negatively charged functional groups; one or more zwitterionic functional groups; or combinations thereof; such that the composition is substantially zwitterionic.

In some embodiments, the positively charged functional groups, the negatively charged functional groups, and/or the zwitterionic functional groups are covalently linked to the biopolymer matrix. In these embodiments, any leaching into the surrounding water can be diminished or eliminated.

In some embodiments, at least one biopolymer matrix comprises at least one zwitterionic biopolymer matrix, itself comprising a combination of at least one positively charged functional group and at least one negatively charged functional group.

In some embodiments, an antifouling composition comprises at least one biopolymer matrix further comprising both a plurality of positively charged functional groups and a plurality of negatively charged functional groups wherein the composition is substantially zwitterionic. In this instance, both positive and negatively charged functional groups can be found on a single polymer (or plurality of polymers) rendering the composition substantially zwitterionic. Such compositions applied to a surface can inhibit or prevent adsorption of bacteria on that particular surface.

In some embodiments, the antifouling composition comprises at least two biopolymer matrices, wherein at least one of the at least two biopolymer matrices has at least one positively charged functional group; and at least one of the at least two biopolymer matrices has at least one negatively charged functional group. In this manner, the substantially zwitterionic nature of the composition is provided via a positively charged polymer and a negatively charged polymer.

In some embodiments, the zwitterionic antifouling composition comprises at least one biopolymer matrix further comprising a plurality of zwitterionic functional groups.

In some embodiments, at least one biopolymer matrix comprises one or more zwitterionic functional groups. As used herein, a "zwitterionic functional group" is meant to indicate a single functional group with a positive and a negative electrical charge at different locations within that same functional group.

In some embodiments, the antifouling composition comprises a plurality of biopolymer matrices together providing the zwitterionic nature of the composition as a whole. This can be accomplished through a combination of any of a polymer having either a positive or negative charge, with either or both of a polymer having both positive and negative charged functional groups, or a polymer having zwitterionic functional groups. Any combination may be employed to provide a substantially zwitterionic in nature combination.

In some embodiments, one of the at least one biopolymer matrix comprises a plurality of zwitterionic functional groups, where the overall charge of the biopolymer matrix is approximately neutral and hence zwitterionic. In some embodiments, the at least one biopolymer matrix comprises a plurality of biopolymer matrices comprising in turn a plurality of positively charged functional groups, and plurality of biopolymer matrices comprising in turn a plurality of negatively charged functional groups, where the overall charge of the combined biopolymer matrices is approximately neutral.

In yet other embodiments, the at least one biopolymer matrix comprises a plurality of zwitterionic functional groups, a plurality of positively charged functional groups and a plurality of negatively charged functional groups, where the overall charge is approximately neutral and hence zwitterionic.

In some embodiments, the at least one positively charged functional group comprises a plurality of positively charged functional groups. In some embodiments, the at least one negatively charged functional group comprises a plurality of negatively charged functional groups. Similarly, the at least one zwitterionic functional group may comprise a plurality of zwitterionic functional groups.

In some embodiments, the zwitterionic compositions described herein need not have an overall neutral charge, although they may. Rather, a broad range of positive and negative charges can be employed without losing effectiveness, so long as both positive and negative charges are present in the composition or material. For example, the positive and negative charges in the composition may be present at a ratio of about 9:1 to about 1:9. In some embodiments, the ratio of positive to negative charges in the composition is about 6:1 to about 1:6. In some embodiments, the ratio of positive to negative charges in the composition is about 3:1 to about 1:3. In some embodiments, the ratio of positive to negative charges in the composition is about 2:1 to about 1:2. In some embodiments, the ratio of positive to negative charges in the composition is about 1.5:1 to about 1:1.5. In some embodiments, the ratio of positive to negative charges in the composition is about 1:1. In some embodiments, the ratio of positive charges to negative charges may be 9:1, 8:1, 7:1, 6:1, 5:1, 4:1, 3:1, 2:1, 1.5:1, 1:1.5, 1:2, 1:3, 1:4, 1:5, 1:6, 1:7, 1:8, or 1:9, and ranges between any two of these.

In some embodiments, mixed charge compositions such as an antifouling composition comprising a plurality of negatively charged functional groups and a plurality of positively charged functional groups with an overall neutral charge may have equivalent effects to an anti-fouling composition comprising a plurality of zwitterionic functional groups on protein adsorption, bacterial adhesion and biofilm formation.

In some embodiments, the biopolymer is selected from the group consisting of lignin, cellulose, hemicellulose, dextrin, a wood-derived biopolymer, or a combination thereof. In some embodiments, the wood-derived polymer can be a substance derived from wood such as wood pulp, refined wood pulp, lignin derivatives, wood rosin, rosin cellulose, modified rosin, rosin gum salts, rosin derivatives or combinations thereof.

The biofuel and paper industries produce large amounts of biomass waste in the form of five and six carbon sugars as well as vast amounts of waste products such as Lignin is a highly cross-linked, heavily aromatic, polymeric product that has little value to these industries, and as such is treated as a waste material. Lignin represents an inexpensive biopolymer that is rich with functional groups made up of phenols and primary and secondary alcohols, as seen in the exemplary generic lignin structure below:

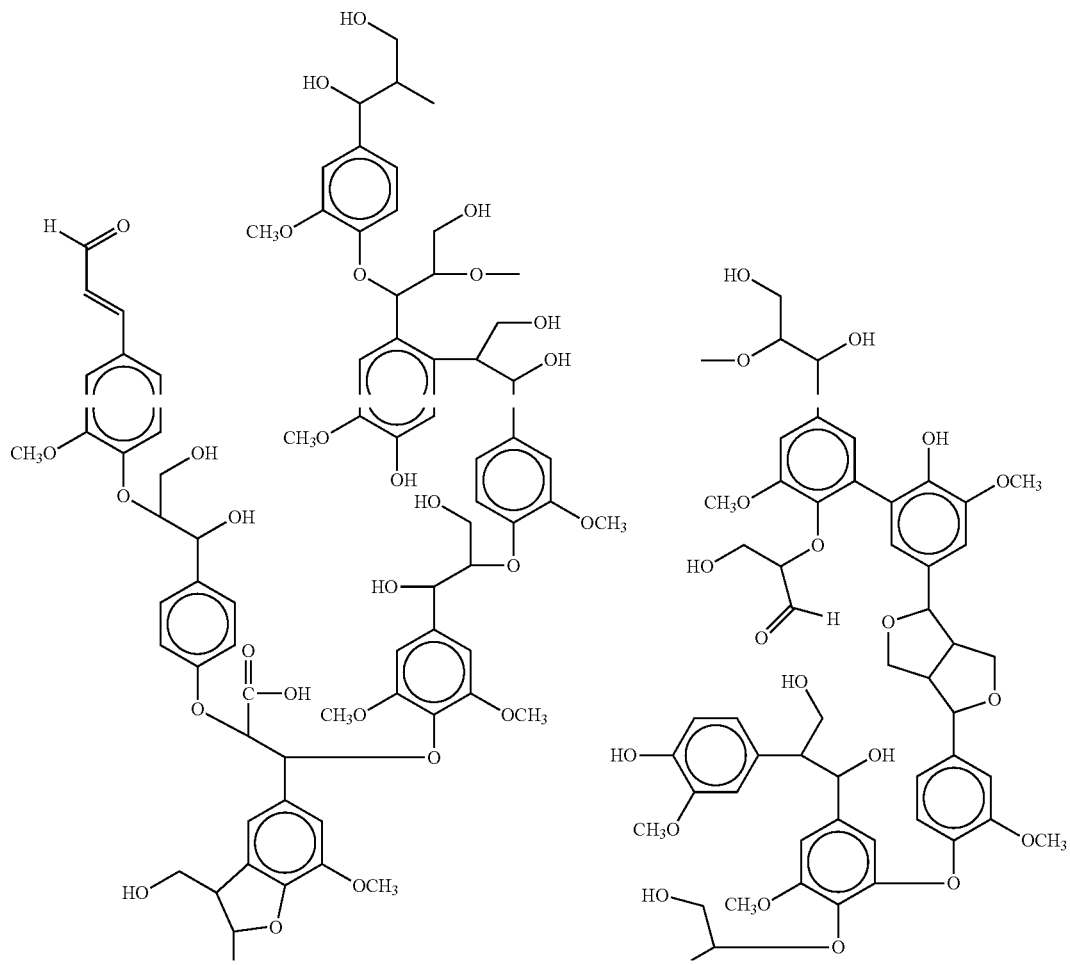

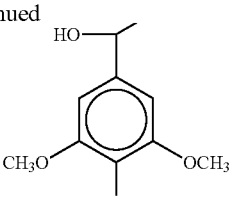
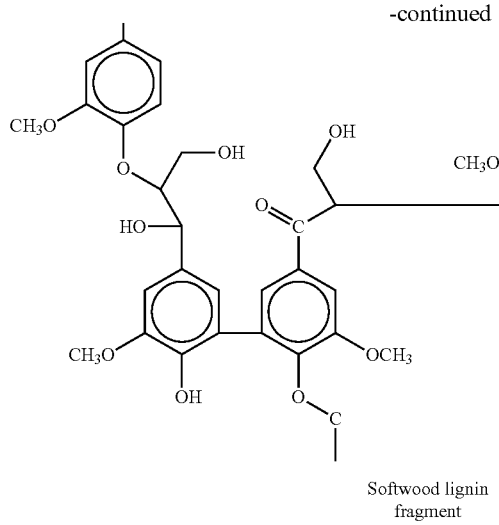

Softwood lignin fragment

In some embodiments, these functional groups represent suitable attachment points for charged or zwitterionic functional groups. In some embodiments, one or more hydroxyl groups of an alcohol, carboxylic acid or phenol are substituted with the one or more positively charged functional groups, and one or more negatively charged functional groups; one or more zwitterionic functional groups; or a mixture thereof.

In some embodiments, the antifouling composition further comprises a base material selected from a paint, lacquer, coating, varnish, stain, or a combination thereof. In some embodiments, the anti-fouling compositions can be combined with base materials with little to no modification to these base materials yet imparting the desired characteristics to the base material. In some embodiments, the antifouling composition has low or no toxicity, or lower toxicity than currently commercially available antifouling materials. In some embodiments, the anti-fouling compositions can be added to base materials with minimal or no modification to existing dispersal techniques.

In further embodiments, antifouling compositions are combined with a base material which is in turn applied to the surface of a vessel. In some embodiments, the base material and the biopolymer matrix are present in a ratio of about 1:1 to about 10,000,000:1. In some embodiments, trace amounts of a biopolymer matrix may be sufficient to prevent, inhibit, delay, alleviate and/or reduce biofouling.

In some embodiments, each of the one or more positively charged functional groups are independently selected from -L-S-Q; wherein S is selected from, $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol; wherein Q is a positively charged moiety selected from —$NR^1R^2R^3$ and $SR^1R^2$; wherein each $R^1$, $R^2$, and $R^3$ is independently selected from H, $C_{1-20}$ alkyl, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide, and oligomers of ethylene glycol; or wherein any two of $R^1$, $R^2$, and $R^3$ may be joined together with the nitrogen to which they are attached to form a $C_{5-7}$ heterocycle; and L is a linker selected from —O—, —C—O—C(O)—N—, —OC(O)O— or —O—C(O)—. In some embodiments, each of one or more positively charged functional groups is a cation.

In some embodiments, the one or more positively charged groups can be derived from a quaternary ammonium salt. Suitable quaternary ammonium salts include, but are not limited to, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, domiphen bromide. While not wishing to be bound by theory, at the molecular level, the quaternary ammonium salts may exert biocidal actions via disruption of intermolecular interactions in the lipid bilayers that make up bacterial cell membranes. This results in loss of structural integrity, loss of permeability controls and in some embodiments, loss of cellular contents resulting in microbial death. In some embodiments, biomolecular complexes become disassociated within the microbial organism.

In some embodiments, the one or more positively charged functional group is selected from the group consisting of benzalkonium, benzethonium, methylbenzethonium, cetalkonium, cetylpyridinium, cetrimonium, cetrimide, dofanium, tetraethylammonium, didecyldimethylammonium, domiphen, and combinations thereof.

A variety of diatom species, a major group of algae, have been exposed to various concentrations of quaternary salts such as benzalkonium chloride, and while there is variation between species, all diatoms were killed at concentrations of less than 0.001%. In some embodiments, only trace amounts of anti-fouling composition would need to be present for high effectiveness.

In some embodiments, the negatively charged functional group is selected from: -$L^2$-$R^4$—Z, wherein Z is a negatively charged moiety selected from —$SO_3$ and —COO; and wherein $R^4$ is selected from $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol of formula —O—(CH$_2$)$_n$OH; and $L^2$ is a linker selected from —O—, C—O—C(O)—N—, —OC(O)O—, and —O—C(O)—.

In some embodiments, the negatively charged functional group comprises a sulfonate anion. In some embodiments, the sulfonate anion comprises p-arylenesulfonate. In some embodiments, a sulfonate anion can be selected from methanesulfonate, trifluoromethanesulfonate, p-toluenesulfonate, benzenesulfonate, or combinations thereof. In some embodiments, a sulfonate anion has the general formula $RSO_2O^-$ wherein R is selected from $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol of formula —O—$(CH_2)_n$OH.

Zwitterionic functional groups comprise a cation and an anion on the same functional group. In some embodiments, the one or more zwitterionic functional groups are selected from: $(NR^1R^2R^3)$—$(CR^5R^6)$n-$(R^7)$, and $(SR^1R^2)$—$(CR^5R^6)$n-$(R^7)$; wherein each $R^1$, $R^2$, and $R^3$ is independently $C_{1-20}$ alkyl of formula, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide; wherein any two of $R^1$, $R^2$, and $R^3$ may be joined together with the nitrogen to which they are attached to form a $C_{5-7}$ heterocycle; wherein each $R^5$ and $R^6$ is independently H, OH, or $C_{1-20}$ alkyl or an oligomer of ethylene glycol; wherein at least one $R^5$ or $R^6$ is a linker selected from —O—, C—O—C(O)—N—, —OC(O)O— or —C(O)O— by which the zwitterion is attached to the biopolymer matrix; wherein $R^7$ is —COO— or —SO$_2$O—; and wherein n is an integer from 1 to 20.

In some embodiments, the zwitterionic functional groups are selected from the group consisting of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof. In some embodiments, the zwitterionic functional groups are selected from the group consisting of chloroformates of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof.

In some embodiments, the zwitterionic functional groups comprise a cephalosporin-based antimicrobial functional group, cefepime, cephaloridine, or a combination thereof. The cephalosporins are a class of β-lactam antibiotics. Cephalosporins are bactericidal and have the same mode of action as other beta-lactam antibiotics (such as penicillins) but are less susceptible to penicillinases. Cephalosporins disrupt the synthesis of the peptidoglycan layer of bacterial cell walls. The peptidoglycan layer is important for cell wall structural integrity. Cephaloridine, a semisynthetic derivative of cephalosporin C exists naturally as a zwitterionic compound.

Some embodiments further comprise at least one polyethylene glycol functional group. In some embodiments, the polyethylene glycol functional group is of the general formula —O—CH$_2$—(CH$_2$—O—CH$_2$—)$_n$—CH$_2$—OH, wherein n is an integer from 1 to 100.

Some embodiments are directed to methods of synthesizing a zwitterionic biopolymer compound, the method comprising: contacting at least one zwitterionic functional group with a biopolymer matrix, wherein the zwitterionic functional group comprises a formula: $(NR^1R^2R^3)$—$(CR^5R^6)$n-$(R^7)$; wherein each $R^1$, $R^2$, and $R^3$ is independently $C_{1-20}$ alkyl, $C_{6-20}$ aryl, $C_{3-20}$ cycloalkane, $C_{1-20}$ allyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide or an oligomer of ethylene glycol; wherein any two of $R^1$, $R^2$, and $R^3$ may be joined together with the nitrogen to which they are attached to form a $C_{5-7}$ heterocycle; wherein each $R^5$ and $R^6$ is independently H, OH, or $C_{1-20}$ alkyl; wherein at least one $R^5$ or $R^6$ is selected from —OH, C—O—C(O)—NH$_2$ or —OC(O)OH; wherein $R^7$ is —COO— or —SO$_2$O—; wherein n is an integer from 1 to 20.

In some embodiments, the zwitterionic functional group is selected from the group consisting of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof. In some embodiments, the zwitterionic functional group comprises a cephalosporin-based antimicrobial functional group, cefepime, cephaloridine, or a combination thereof. In some embodiments, the zwitterionic functional groups are selected from the group consisting of chloroformates of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof.

In some embodiments, the biopolymer is selected from the group consisting of lignin, cellulose, hemicellulose, dextrin, or a combination thereof. Some embodiments further comprise dissolving the biopolymer matrix in a polar aprotic solvent to form a dissolved biopolymer matrix prior to combining with the zwitterionic functional group. In some embodiments, the polar aprotic solvent is selected from the group consisting of dimethylsulfoxide, dimethylformamide, dimethylacetamide, N-methyl-2-pyrrolidone, dichloromethane, tetrahydrofuran, ethyl acetate, acetone, acetonitrile, hexamethylphosphoramide, and combinations thereof.

Some embodiments further comprise adding a proton sponge to the polar aprotic solvent prior to dissolving the biopolymer matrix. In some embodiments, the proton sponge is selected from the group consisting of pyridine, 1,8-bis(dimethylamino)naphthalene, 1,8 bis(hexamethyltriaminophosphazenyl)naphthalene, and combinations thereof. In some embodiments, the proton sponge is removed from the polar aprotic solvent containing the dissolved biopolymer matrix by base washing, base extraction, distillation or a combination thereof.

In some embodiments, the zwitterionic biopolymer compound is dried to form a powder. In some embodiments, the zwitterionic biopolymer compound is dried by evaporating off the polar aprotic solvent, to form a powder.

In some embodiments, any pair of molecules comprising a positively or negatively charged functional group linked via a variable length alkyl chain to an alcohol group may be suitable for synthesizing a zwitterionic biopolymer compound.

The negatively charged functional group comprises the formula -$L^2$-$R^4$—Z, wherein Z is a negatively charged moiety selected from —SO$_3$ and —COO; and wherein $R^4$ is selected from $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol of formula —O—$(CH_2)_n$OH; and $L^2$ is a linker selected from —O—, C—O—C(O)—N—, —OC(O)O—, and —O—C(O)—.

The positively charged functional group comprises the formula -L-S-Q wherein S is selected from, $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol; wherein Q is a positively charged moiety selected from —$NR^1R^2R^3$ and $SR^1R^2$; wherein each $R^1$, $R^2$, and $R^3$ is independently selected from H, $C_{1-20}$ alkyl, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3, 3-tetramethyl-butyl)-benzene, N-phenyl-acetamide, and oligomers of ethylene glycol; or wherein any two of $R^1$, $R^2$, and $R^3$ may be joined together with the nitrogen to which they are attached to form a $C_{5-7}$ heterocycle; and L is a linker selected from —O—, —C—O—C(O)—N—, —OC(O)O— or —O—C(O)—.

Some embodiments are directed to methods of synthesizing a zwitterionic biopolymer compound, the method comprising: providing at least one positively charged chloroformate; providing at least one negatively charged chloroformate; and contacting the at least one positively charged chloroformate and the at least one negatively charged chloroformate with a biopolymer matrix to form a biopolymer compound comprising at least one positively charge functional group and at least one negatively charged functional group.

In some embodiments, the positive and negatively charged chloroformates are prepared according to the following reaction scheme:

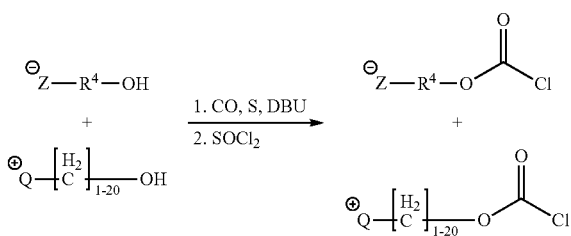

In some embodiments, the at least one positively charged chloroformate is prepared by: contacting a positively charged compound of formula: HO—($C_{1-20}$)alkyl-Q with carbon monoxide, sulphur, 1,8-diazabicyclo[5.4.0]undec-7-ene, or a combination thereof followed by treatment with sulfuryl chloride to form a chloroformate of the formula: Cl—C(O)—O—($C_{1-20}$)alkyl-Q, wherein Q is a positively charged moiety selected from $NR^1R^2R^3$ wherein $R^1$, $R^2$, and $R^3$ are independently $C_{1-20}$ alkyl, $C_{6-20}$ aryl, $C_{3-20}$ cycloalkanes, $C_{1-20}$ alkyl acetamide of formula $C_nH(2_{n+1})$—C(O)—N(CH$_2$)$_2$, alkyloxybenzene, methoxy benzene, (2-ethoxy-ethoxy)-4-(1,1,3,3-tetramethyl-butyl)-benzene, and N-phenyl-acetamide; and wherein $R^1$, $R^2$, and $R^3$ may be joined together with the nitrogen to which they are attached to form a $C_{5-7}$ heterocycle.

In some embodiments, the biopolymer compound is a biocide. As used herein, the term "biocide" is intended to mean a chemical or biological substance or microorganism which can deter, render harmless, or exert a controlling effect on any harmful organism by chemical or biological means. In some embodiments, a biocide can prevent, inhibit, delay, alleviate and/or reduce formation of bacterial colonies. In some embodiments, a biocide can prevent, inhibit, delay, alleviate and/or reduce the biological growth and infestation. In some embodiments, a biocide may control or prevent, inhibit, delay, alleviate and/or reduce the growth of bacteria on a surface.

In some embodiments, the positively charged compound is a quaternary ammonium salt. In some embodiments, Q is selected from the group consisting of benzalkonium, benzethonium, methylbenzethonium, cetalkonium, cetylpyridinium, cetrimonium, cetrimide, dofanium, tetraethylammonium, didecyldimethylammonium, domiphen, and combinations thereof.

In some embodiments, the at least one negatively charged chloroformate is prepared by: contacting a negatively charged compound of formula: HO—$R^4$—Z with carbon monoxide, sulphur, 1,8-diazabicyclo[5.4.0]undec-7-ene, or a combination thereof followed by treatment with sulfuryl chloride to form a chloroformate of the formula: Cl—C(O)— O—$R^4$—Z, wherein Z is a negatively charged moiety selected from —SO$_3$ and —COO; and wherein $R^4$ is a bond, $C_{1-20}$ alkyl or arylene. In some embodiments, Z comprises a sulfonate anion. In some embodiments, the sulfonate anion is p-arylenesulfonate.

In some embodiments, an acid chloride of positively charged compound and an acid chloride of the negatively charged compound can be used. In some embodiments, an acid chloride containing a positively charged fragment may react with the alcohol groups on the biopolymer.

In some embodiments, the positively charged chloroformates and the negatively charged chloroformates are present in a ratio of about 1:9 to about 9:1. In some embodiments, the positively charged chloroformates and the negatively charged chloroformates are present in a ratio of about 1:1.

In some embodiments, the biopolymer matrix is selected from the group consisting of lignin, cellulose, hemicellulose, dextrin, and combinations thereof. Some embodiments further comprise dissolving the biopolymer matrix in a polar aprotic solvent to form a dissolved biopolymer matrix prior to reacting with the at least one positively charged chloroformates and the at least one negatively charged chloroformates. In some embodiments, the polar aprotic solvent is selected from the group consisting of dimethylsulfoxide, dimethylformamide, dimethylacetamide, N-methyl-2-pyrrolidone, dichloromethane, tetrahydrofuran, ethyl acetate, acetone, acetonitrile, hexamethylphosphoramide, and a combination thereof.

Some embodiments further comprise adding a proton sponge to the polar aprotic solvent prior to dissolving the biopolymer matrix. In some embodiments, the proton sponge is selected from the group consisting of pyridine, 1,8-bis(dimethylamino)naphthalene, 1,8 bis(hexamethyltriaminophosphazenyl)naphthalene, and combinations thereof. In some embodiments, the proton sponge is removed from the polar aprotic solvent containing the dissolved biopolymer matrix by base washing, base extraction, distillation or a combination thereof.

Some embodiments further comprise contacting the at least one positively charged chloroformates and the at least one negatively charged chloroformates with the dissolved biopolymer matrix to form the zwitterionic biopolymer compound. The abundance of free hydroxyl groups in the biopolymer may react readily with the chloroformates to form stable carbonate linkages. In some embodiments, this results in a biopolymer with at least one hydroxyl group replaced with a positively charged functional group and at least one hydroxyl group with a negatively charged functional group. In some embodiments, the resulting biopolymer comprises a plurality of positively charged functional groups and a plurality of negatively charged functional groups. In some embodiments, the overall charge of the resulting biopolymer is approximately neutral. In some embodiments, the overall charge is linked to the ratio of positively charged functional groups to negatively charged functional groups. In some embodiments, the positively charged functional groups and the negatively charged functional groups are present in a ratio of about 1:9 to about 9:1. In some embodiments, the positively charged functional groups and the negatively charged functional groups are present in a ratio of about 1:1.

In some embodiments, the zwitterionic biopolymer compound is dried to form a powder. In some embodiments, the zwitterionic biopolymer compound is dried by evaporating off the polar aprotic solvent, to form a powder.

In some embodiments, the positively charged functional group comprises 2-(trimethylammonium chloride) ethanol and the negatively charged functional group comprises 3-sulphopropyl. Some embodiments further comprise contacting 2-(trimethylammonium chloride) ethanol and 3-sulphoproyl potassium salt with carbon monoxide, sulphur, 1,8-diazabicyclo[5.4.0]undec-7-ene, or a combination thereof followed by treatment with sulfuryl chloride to form chloroformates of 2-(trimethylammonium chloride) ethanol and 3-sulphoproyl.

In some embodiments, the chloroformate of 2-(trimethylammonium chloride) ethanol and the chloroformate of 3-sulphoproyl is present in a stoichiometric ratio of about 1:1.

In some embodiments, the biopolymer matrix is lignin. Some embodiments further comprise dissolving the lignin in dimethylsulfoxide, pyridine or a combination thereof prior to combining with the at least one positively charged chloroformates and the at least one negatively charged chloroformates. Dimethyl sulfoxide is a solvent known to be a good solvent for dissolving biopolymers such as lignin.

Some embodiments are directed to methods of protecting a surface from the formation of a biofilm, the method comprising: providing a zwitterionic biopolymer matrix having at least one functional group selected from both positively charged and negatively charged functional groups, zwitterionic functional groups, polyethylene glycol functional groups or a combination thereof; combining the zwitterionic biopolymer matrix with a base selected from paint, coating, varnish, stain, or a combination thereof; coating the surface with the mixture; and allowing the mixture to cure or dry, whereby the cured mixture will reduce the formation of a biofilm on the surface. In some embodiments, the surface is the hull of a ship.

In some embodiments, surface is selected from an automotive part, an automotive body panel, an amphibious vehicle part, an amphibious vehicle body panel, an aircraft part, an aircraft body panel, a turbine, a fan, an air conditioner, an air conditioner part, a refrigeration unit, a refrigeration unit part, a humidifier, a humidifier part, a dehumidifier, a dehumidifier part, a cooling tower, a cooling tower part, a water storage tank, a water storage tank part, a water storage container, a tanker, a hose, a hose fitting, a vent, ductwork, a pipe, a tube, a plumbing part, a plumbing tool, a swimming pool, swimming pool equipment, a ceramic tile, a glass window pane, a plastic window pane, hospital equipment, culinary equipment or a textile, a spa, a shower, a bathtub, a sink, a porcelain tile, a faucet, a shower curtain, a drain, a sewer, a kitchen counter, a kitchen cabinet, a food preparation area, a surface in a hospital setting, sports and recreation equipment, food processing and handling machinery, a business machine, a consumer appliance, a general household good, a transportation interior, construction supplies, a medical device, a pair of forceps, a clamp, an occluder, a retractor, a distractor, a scalpel, a lancet, a drill bit, a rasp, a trocar, a ligature, a dilator, a specula, a suction tip, a suction tube, a tyndaller, a drill, a dermatome, a scope, a probe, an endoscope, a tactile probe, a carrier, an applier, an ultrasound tissue disruptor, a cryotome, a laser cutting guide, a measurement device, a caliper, a stent, a catheter, a guide wire, a denture, a bridge, a crown, a pin, a rod, a screw, a plate, a prosthetic, a hip joint, a pacemaker, a cochlear implant and a drug eluting stent.

As used herein, the term "cure" is intended to mean the toughening or hardening of a material. In some embodiments, "cure" includes the process of drying, whereby a material loses water gradually such that the material becomes free from liquids and moisture.

Some embodiments are methods of treating the hull surface of a marine vessel to make it less attractive to the hydrophobic biological adhesive employed by many parasitic macrofouling species.

The first step in the biofouling process involves the surface of a vessel coming into contact with water and becoming wet. In some embodiments, a vessel may come into contact with salt water, fresh water or combinations thereof. In some embodiments, the entire surface area of the vessel which may be exposed to water is susceptible to biofouling.

Macrofouling species such as barnacles and mussels secrete protein adhesives that are hydrophobic in nature. In some embodiments, a zwitterionic surface may repel a hydrophobic protein adhesive.

In some embodiments, the a zwitterionic polymer matrix, may prevent, inhibit, delay, alleviate and/or reduce biofouling with a biocidal action which may prevent, inhibit, delay, alleviate and/or reduce the initial biofilm formation and by providing a hydrophilic surface that repels macrofouling.

Some embodiments are directed to a coating composition comprising: a base material selected from a coating, paint, lacquer, varnish, stain, or a combination thereof; and a zwitterionic biopolymeric matrix.

In some embodiments, once the zwitterionic biopolymer compound is synthesized or otherwise provided, it can then be mixed into standard base material formulations for application to the hull of a vessel. The zwitterionic biopolymer compound will adhere to the hull of the vessel once the paint or varnish has dried or cured.

In some embodiments, the zwitterionic biopolymer matrix and the base material is present in a ratio of about 1:1 to about 1:10,000,000. In some embodiments, the zwitterionic biopolymer matrix and the base material is present in a ratio of about 1:1 to about 1:10, about 1:10 to about 1:100, about 1:100 to about 1:1000, about 1:1000 to about 1:10,000, about 1:10,000 to about 1:100,000, about 1:100,000 to about 1:1,000,000, about 1:1,000,000 to about 1:10,000,000. In some embodiments, the kinetics of polymer diffusion would ensure a much slower process of additive leakage than the small molecule tin compounds or copper complexes that are currently used as biocides for biofouling protection.

Although embodiments presented herein are focused on providing protection to a surface from marine biofouling, certain embodiments can also be applied to surfaces to prevent microfouling and biofilm formation in general.

In some embodiments, the zwitterionic antifouling compositions, zwitterionic biopolymer compounds or combinations thereof described herein can be combined with existing coatings, paints, lacquers, varnishes, stains, or combinations thereof an applied to almost any surface that the coating, paint, lacquer, varnish, stain, or a combination thereof would normally be applied to.

In some embodiments, the zwitterionic antifouling compositions, zwitterionic biopolymer compounds or combinations thereof described herein can be combined with existing coatings, paints, lacquers, varnishes, stains, or combinations thereof an applied to a surface that will be exposed to water, moisture, humidity, water vapor, steam, condensation or ice. In some embodiments, these surfaces include but are not limited to the surfaces of automotive parts and body panels, parts and body panels of amphibious vehicles, aircraft parts and body panels, turbines, fans, air conditioners, refrigeration units and parts, humidifiers, dehumidifiers, cooling towers, water storage tanks and containers, tankers, hoses and fittings, vent and ductwork, pipes and tubes, plumbing parts and tools, swimming pool equipment, ceramic tiles, glass and plastic window panes, hospital equipment, culinary equipment or textiles. In some embodiments, individual components making up the surfaces described herein can be coated. In some embodiments, the finished product is coated.

In some embodiments, the zwitterionic antifouling compositions, zwitterionic biopolymer compounds or combinations thereof described herein can be applied directly to the surfaces of swimming pools, spas, showers, bathtubs, sinks, ceramic and porcelain tile, plumbing, faucets, shower curtains, pipes drains and sewers. In some embodiments, the zwitterionic antifouling compositions, zwitterionic biopolymer compounds or combinations thereof described herein can be directly applied to any surface that is exposed to water in it course of usage. In some embodiments, the zwitterionic antifouling compositions, zwitterionic biopolymer compounds or combinations thereof described herein can be used to coat surfaces such as but not limited to kitchen counters and cabinets, food preparation areas, surfaces in a hospital setting such as handles and countertops.

In some embodiments, examples of finished products, the surfaces of which could be coated with the zwitterionic antifouling compositions, zwitterionic biopolymer compounds or combinations thereof described herein include but are not limited to sports and recreation equipment, food processing and handling machinery business machines and consumer appliances, general household goods, transportation interiors, construction supplies and medical devices.

In some embodiments, the zwitterionic antifouling compositions, zwitterionic biopolymer compounds or combinations thereof described herein can be applied directly to a surface in the form of a coating. In some embodiments, suitable surfaces include metallic, ceramic, glass and organic surfaces.

In some embodiments, the zwitterionic antifouling compositions, zwitterionic biopolymer compounds or combinations thereof described herein can be applied directly to a metal surface. Suitable metallic substrates include but are not limited to any of the common structural metals including, but not limited to, iron, steel, including stainless steel, lead, aluminum, copper, brass, bronze, Monel metal, nickel, titanium and zinc. Suitable metals also include precious metals such as but not limited to gold, silver, palladium, rhodium, iridium, osmium, ruthenium, germanium, beryllium, gallium, indium, tellurium and platinum.

In some embodiments, the zwitterionic antifouling compositions, zwitterionic biopolymer compounds or combinations thereof described herein can be applied directly to a mineral surface. In some embodiments, mineral surfaces include but are not limited to diamond, sapphire, crystal, tanzanite, ruby, quartz, topaz, and amethyst.

In some embodiments, the zwitterionic antifouling compositions, zwitterionic biopolymer compounds or combinations thereof described herein can be applied directly to a plastic surface. Suitable plastic surfaces include but are not limited to those made up of polyester, polyethylene terephthalate, polyethylene, high-density polyethylene, polyvinyl chloride, polyvinylidene chloride, low-density polyethylene, polypropylene, polystyrene, high impact polystyrene, polyamides, acrylonitrile butadiene styrene, polycarbonate, polycarbonate acrylonitrile butadiene styrene, polyurethanes, melamine formaldehyde, plastarch material, phenolics, polyetheretherketone, polyetherimide, polylactic acid, polymethyl methacrylate, polytetrafluoroethylene, urea-formaldehyde or nylon.

In some embodiments, the zwitterionic antifouling compositions, zwitterionic biopolymer compounds or combinations thereof described herein can be applied directly to an organic surface or material. In some embodiments, organic surfaces or material include, but are not limited to, leather and all common textile materials such as polyester, polyamide, rayon and cotton fabrics and cords. Suitable textile substrates also include, but are not limited to, glass fibers or filaments.

In some embodiments, the zwitterionic antifouling compositions, zwitterionic biopolymer compounds or combinations thereof described herein can be applied directly to an elastomeric surface or material. In some embodiments, elastomeric surfaces or materials include but are not limited to, natural rubber, styrene butadiene rubber of both high and low durometer grades and oil extended types, neoprene (G and W types), butyl runner, chlorobutyl rubber, ethylene-propylene terpolymer rubber, butadiene-acrylonitrile rubber, chlorosulfonated polyethylene rubber, polyurethane rubber, polyacrylate rubber and ethylene-propylene copolymer rubber. In some embodiments the zwitterionic antifouling compositions, zwitterionic biopolymer compounds or combinations thereof described herein can be combined with an elastomeric material. In some embodiments the zwitterionic antifouling compositions, zwitterionic biopolymer compounds or combinations thereof described herein are integrated into an organic polymer thereby conferring anti-fouling properties, biocidal properties or a combination thereof to the elastomeric material. In some embodiments, the zwitterionic antifouling compositions, zwitterionic biopolymer compounds or combinations thereof described herein can be combined with an organic polymer. In some embodiments the zwitterionic antifouling compositions, zwitterionic biopolymer compounds or combinations thereof described herein are integrated into an organic polymer thereby conferring antifouling and biocidal properties to the organic polymer. In some embodiments, the organic polymer can be synthetic of natural. Suitable organic polymers include but are not limited to polyester, polyethylene terephthalate, polyethylene, high-density polyethylene, polyvinyl chloride, polyvinylidene chloride, low-density polyethylene, polypropylene, polystyrene, high impact polystyrene, polyamides, acrylonitrile butadiene styrene, polycarbonate, polycarbonate acrylonitrile butadiene styrene, polyurethanes, melamine formaldehyde, plastarch material, phenolics, polyetheretherketone, polyetherimide, polylactic acid, polymethyl methacrylate, polytetrafluoroethylene, urea-formaldehyde or nylon.

In some embodiments, the zwitterionic antifouling compositions, zwitterionic biopolymer compounds or combinations thereof described herein can be used to coat medical devices, surgical devices, and implants. In some embodiments, the zwitterionic antifouling compositions, zwitterionic biopolymer compounds or combinations thereof described herein can be combined with existing coatings or applied directly to the surface. In some embodiments, the zwitterionic antifouling compositions, zwitterionic biopolymer compounds or combinations thereof described herein can be integrated into the material making up the medical device, surgical device, or implant. In some embodiments integrating the zwitterionic antifouling compositions, zwitterionic biopolymer compounds or combinations thereof described herein into the material may confer anti-fouling properties, biocidal properties or a combination thereof. In some embodiments, examples of medical and surgical devices include but are not limited to forceps, clamps and occluders, retractors, distractors, scalpels, lancets, drill bits, rasps, trocars, ligatures, dilators, specula, suction tips and tubes, tyndallers, drills, dermatomes, scopes, probes, endoscopes, tactile probes, carriers, appliers, ultrasound tissue disruptors, cryotomes, laser cutting guides, measurement devices, calipers, stents, catheters, or guide wires.

In some embodiments, examples of implants include dental implants such as but not limited to dentures, bridges and crowns. In some embodiments, examples of implants include surgical implants such as but not limited to pins, rods, screws, plates, and prosthetics such as hip joints, pacemakers, cochlear implants or drug eluting stents.

In some embodiments, the zwitterionic antifouling compositions, zwitterionic biopolymer compounds or combinations thereof described herein can be used to coat wound dressings or bandages. In some embodiments, the fibers making up these products can be coated. In some embodiments, the finished product can be coated. In some embodiments, the dressing or bandage will have anti-fouling properties, biocidal properties or a combination thereof.

EXAMPLES

Example 1

Synthesizing a Zwitterionic Biopolymer Compound Having 3-Sulphopropyl and 2-(trimethylammonium) Functional Groups A zwitterionic biopolymer antifouling composition is prepared by a multistep process comprising first synthesizing a biopolymer matrix having both positive and negative functional groups. This may be done by first preparing positive and negatively charged chloroformates as shown below. All the steps in this process are performed at room temperature.

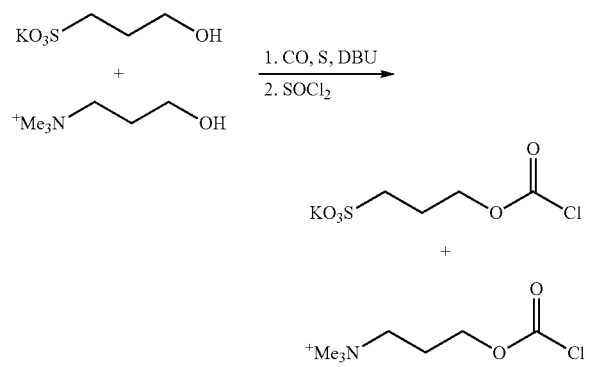

The preparation of the negatively charged chloroformate is performed by treating 3-sulphopropyl potassium salt with carbon monoxide and sulphur in 1,8-Diazabicycloundec-7-ene (DBU) to yield a S-methyl-O-phenyl carbonthioate and reacting the resultant S-methyl-O-phenyl carbonthioate with sulfuryl chloride to form a 3-sulphopropyl chloroformate.

The preparation of the positively charged chloroformate is performed by treating 2-(trimethylammonium chloride) ethanol with carbon monoxide and sulphur in 1,8-Diazabicycloundec-7-ene (DBU) and reacting the resultant compound with sulfuryl chloride to form a 2-(trimethyl ammonium) chloroformate. Both reactions are allowed to proceed at room temperature for about 1 hour to about 4 hours.

The zwitterionic biopolymer compound is prepared by mixing the positively charged and negatively charged chloroformates in a 1:1 stoichiometric ratio in excess with lignin that is dissolved in dimethyl sulfoxide (DMSO), in the presence of pyridine to act as a proton sponge, to yield a lignin derivative decorated with a plurality of positively charged functional groups and a plurality of negatively charged functional groups that are collectively zwitterionic. The lignin derivative is then allowed to dry by evaporating the DMSO to form a powder.

Once the zwitterionic biopolymer compound is synthesized, it can then be mixed into standard paint or varnish formulations for application to the hull of a vessel or other surface that might be subject to biofouling. Given potency of the zwitterionic polymer compound, it can be mixed with the paint or varnish at a ratio of 1 part zwitterionic biopolymer compound to 10,000 parts paint or varnish. Once the paint or varnish has dried or cured, it will permanently adhere the zwitterionic biopolymer compound to the hull of the vessel or other surface that might be subject to biofouling.

Example 2

Synthesizing a Zwitterionic Composition Comprising a Positively Charges Biopolymer and a Separate Negatively Charged Biopolymer A zwitterionic antifouling composition is prepared by first synthesizing a biopolymer matrix having both positive and negative functional groups by separately preparing positive and negatively charged chloroformates as shown below.

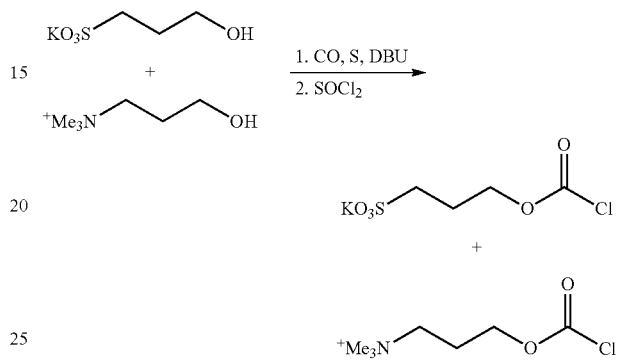

Preparation of the negatively charged chloroformate is prepared by treating 3-sulphopropyl potassium salt with carbon monoxide and sulphur in 1,8-Diazabicycloundec-7-ene (DBU) to yield a S-methyl-O-phenyl carbonthioate and reacting the resultant S-methyl-O-phenyl carbonthioate with sulfuryl chloride to form a 3-sulphopropyl chloroformate.

Preparation of the positively charged chloroformate is performed by treating 2-(trimethylammonium chloride) ethanol with carbon monoxide and sulphur in 1,8-Diazabicycloundec-7-ene (DBU) and then reacting the resultant compound with sulfuryl chloride to form a 2-(trimethyl ammonium) chloroformate. Both reactions are allowed to proceed at room temperature for about 1 hour to about 4 hours.

Preparation of the negatively charged biopolymer compound is performed by mixing the negatively charged chloroformate in excess with lignin that is dissolved in dimethyl sulfoxide (DMSO), in the presence of pyridine to act as a proton sponge to yield a lignin derivative decorated with a plurality of negatively charged functional groups.

Preparation of the positively charged biopolymer compound is performed by mixing the positively charged chloroformate in excess with lignin that is dissolved in dimethyl sulfoxide (DMSO), in the presence of pyridine to act as a proton sponge to yield a lignin derivative decorated with a plurality of positively charged functional groups.

Once the negatively charged biopolymer compound and the positively charged biopolymer compound are synthesized, they are combined in a 1:1 stoichiometric ratio to form a zwitterionic composition comprising a positively charges biopolymer and a separate negatively charged biopolymer. The resulting biopolymers are then allowed to dry to form a powder.

The zwitterionic composition comprising a positively charges biopolymer and a separate negatively charged biopolymer it can then be mixed into standard paint or varnish formulations for application to the hull of a vessel or other surface that might be subject to biofouling. Given potency of the zwitterionic composition, it can be mixed with the paint or varnish at a ratio of 1 part zwitterionic composition to 10,000 parts paint or varnish. Once the paint or varnish has dried or cured, it will permanently adhere the zwitterionic composition to the hull of the vessel or other surface that might be subject to biofouling.

Example 3

Synthesizing a Zwitterionic Biopolymer Compound Having Zwitterionic Functional Groups The method comprises first dissolving lignin in dimethylsulfoxide containing pyridine, 1,8-bis(dimethylamino)naphthalene to form a dissolved lignin and then combining the dissolved lignin with a chloroformate of a zwitterionic compound selected from a sulfobetaine acrylate, a sulfobetaine acrylamide, a sulfobetaine vinyl compound, a sulfobetaine epoxide, a sulfobetaine methacrylate, a carboxybetaine acrylate, a carboxybetaine acrylamide, a carboxybetaine vinyl compound, a carboxybetaine epoxide, a carboxybetaine methacrylate, a cephalosporin-based antimicrobial functional group, a cefepime, a cephaloridine, or a combination thereof.

Once the zwitterionic biopolymer compound is synthesized, it can then be dried to form a powder and mixed into standard paint or varnish formulations for application to the hull of a vessel or other surface that might be subject to biofouling. Given potency of the zwitterionic polymer compound, it can be mixed with the paint or varnish at a ratio of 1 part zwitterionic biopolymer compound to 10,000 parts. Once the paint or varnish has dried or cured, it will permanently adhere the zwitterionic biopolymer compound to the hull of the vessel or other surface that might be subject to biofouling.

Example 4

Preparation of Antifouling Paint

First a zwitterionic biopolymer compound is combined with marine grade paint prior to application of the paint to the surface of a vessel. The zwitterionic biopolymer compound is then mixed with the paint in a ratio of 1 gram of compound for each gallon of paint prepared.

Example 5

Application of Anti-Fouling Paint to a Marine Vessel

Once a zwitterionic biopolymer compound has been mixed with a marine grade paint, the paint is mixed to ensure distribution of the compound and applied according to the manufacturer's instructions to the surface to be painted, in this case the hull of a marine vessel. The paint is then allowed to dry according to the manufacturer's instructions. Once dry the zwitterionic biopolymer compound will be permanently present in the dried paint and provide biocidal and antifouling properties to the paint coating.

In the present disclosure, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURE, can be arranged, substituted, combined, separated, and designed in a wide variety of different configurations, all of which are explicitly contemplated herein.

Example 6

Application of Antifouling Coating to a Surface to be Exposed to Water

The zwitterionic biopolymer compound of example 3 can be applied directly to a surface that will be exposed to water and therefore to microfouling. The completed zwitterionic biopolymer compound is applied to the surface for which protection from bio-fouling is desired. Once applied the zwitterionic biopolymer compound is allowed to dry forming a protective layer on the surface. This type of application is particularly well suited to protect from bio-fouling surfaces such as automotive parts and body panels, parts and body panels of amphibious vehicles, aircraft parts and body panels, turbines, fans, air conditioners, refrigeration units and parts, humidifiers, dehumidifiers, cooling towers, water storage tanks and containers, tankers, hoses and fittings, vent and ductwork, pipes and tubes, plumbing parts and tools, swimming pool equipment, ceramic tiles, glass and plastic window panes, hospital equipment, culinary equipment or textiles. These surfaces are frequently exposed to water, moisture, humidity, water vapor, steam, condensation or ice.

Application of the zwitterionic biopolymer compound coating is performed prior to the surfaces first exposure to water, moisture, humidity, water vapor, steam, condensation or ice and allowed to cure completely prior to exposure. Additional coatings with the zwitterionic biopolymer compound coating can be provided over time.

In applications where it is generally standard practice to paint, coat, lacquer, varnish or stain a surface, the zwitterionic biopolymer compound can be combined with the paint, coat, lacquer, varnish or stain prior to application to the surface to be protected.

Application of the zwitterionic biopolymer compound either as a stand-alone coating or in combination with a paint, coat, lacquer, varnish or stain may reduce or attenuate microfouling, bio-fouling or where the surface is exposed to a marine ecosystem, macrofouling.

Example 7

Combining the Zwitterionic Biopolymer Compound with an Organic Polymer to Form an Organic Polymer with Anti-Fouling Properties The zwitterionic biopolymer compound of example 3 can be combined with an organic polymer. The resulting organic polymer may have anti-fouling or biocidal properties due to the presence of the zwitterionic biopolymer compound. Suitable organic polymers include polyester, polyethylene terephthalate, polyethylene, high-density polyethylene, polyvinyl chloride, polyvinylidene chloride, low-density polyethylene, polypropylene, polystyrene, high impact polystyrene, polyamides, acrylonitrile butadiene styrene, polycarbonate, polycarbonate acrylonitrile butadiene styrene, polyurethanes, melamine formaldehyde, plastarch material, phenolics, polyetheretherketone, polyetherimide, polylactic acid, polymethyl methacrylate, polytetrafluoroethylene, urea-formaldehyde or nylon.

The zwitterionic biopolymer compound can be combined with an organic polymer during the manufacturing stages of the polymer or during the manufacturing of the finished product containing the organic polymer. Examples of these finished products include but are not limited to sports and recreation equipment, food processing and handling machinery business machines and consumer appliances, general household goods, transportation interiors, construction supplies and medical devices. The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed is:

1. An anti-fouling coating composition comprising:
    at least one biopolymer matrix comprising a lignin having one or more zwitterionic functional groups, one or more positively charged functional groups, and one or more negatively charged functional groups such that the composition is substantially zwitterionic.

2. The anti-fouling coating composition of claim 1, further comprising a base material selected from a paint, lacquer, coating, varnish, stain, or a combination thereof.

3. The anti-fouling coating composition of claim 1, wherein the lignin comprises two or more hydroxyl groups of an alcohol, carboxylic acid or phenol substituted with:
    the one or more positively charged functional groups;
    the one or more negatively charged functional groups; and
    the one or more zwitterionic functional groups.

4. The anti-fouling coating composition of claim 3, wherein the zwitterionic functional groups are selected from the group consisting of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof.

5. The anti-fouling coating composition of claim 3, wherein the zwitterionic functional groups comprise a cephalosporin-based antimicrobial functional group, cefepime, cephaloridine or a combination thereof.

6. The anti-fouling coating composition of claim 1, wherein each of the one or more positively charged functional groups is independently selected from -L-S-$Q^{\oplus}$;
    wherein S is selected from, $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol;
    wherein Q is a positively charged moiety selected from —$N^{\oplus}R^1R^2R^3$ and $S^{\oplus}R^1R^2$, wherein each $R^1$, $R^2$, and $R^3$ is independently selected from H, $C_{1-20}$ alkyl, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide, and oligomers of ethylene glycol or wherein any two of $R^1$, $R^2$, and $R^3$ may be joined together with the nitrogen to which they are attached to form a $C_{5-7}$ heterocycle; and L is a linker selected from —O—, —C—O—C(O)—N—, —OC(O)O— or —O—C(O)—.

7. The anti-fouling coating composition of claim 1, wherein the one or more positively charged functional group is selected from the group consisting of benzalkonium, benzethonium, methylbenzethonium, cetalkonium, cetylpyridinium, cetrimonium, cetrimide, dofanium, tetraethylammonium, didecyldimethylammonium, domiphen, and combinations thereof.

8. The anti-fouling coating composition of claim 1, wherein the negatively charged functional group is selected from: -L$^2$-R$^4$—Z$^\ominus$, wherein $Z^\ominus$ is a negatively charged moiety selected from —SO$_3^\ominus$ and —COO$^\ominus$;

wherein $R^4$ is selected from $C_{1-20}$ alkyl, $C_{6-18}$ aryl, $C_{1-20}$ arylene, $C_{6-20}$ aryl, $C_{3-20}$ cycloalkane, $C_{1-20}$ alkyloxybenzene, methoxy benzene, (2-ethoxy-ethoxy)-4-(1,1,3,3-tetramethyl-butyl)-benzene, benzene, a carbohydrate and an oligomer of ethylene glycol of formula —O—(CH$_2$)$_n$OH; and $L^2$ is a linker selected from —O—, C—O—C(O)—N—, —OC(O)O—, and —O—C(O)—.

9. The anti-fouling coating composition of claim 1, wherein the negatively charged functional group comprises a sulfonate anion.

10. The anti-fouling coating composition of claim 1, wherein the one or more zwitterionic functional groups are selected from: ($^\oplus$NR$^1$R$^2$R$^3$)—(CR$^5$R$^6$)$_n$—(R$^{7\ominus}$), and ($^\oplus$SR$^1$R$^2$)—(CR$^5$R$^6$)$_n$—(R$^{7\ominus}$);

wherein each $R^1$, $R^2$, and $R^3$ is independently $C_{1-20}$ alkyl of formula, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide;

wherein any two of $R^1$, $R^2$, and $R^3$ may be joined together with the nitrogen to which they are attached to form a $C_{5-7}$ heterocycle;

wherein each $R^5$ and $R^6$ is independently H, OH, or $C_{1-20}$ alkyl or an oligomer of ethylene glycol;

wherein at least one $R^5$ or $R^6$ is a linker selected from —O—, C—O—C(O)—N—, —OC(O)O— and —C(O)O— by which the zwitterion is attached to the biopolymer matrix;

wherein $R^7$ is —COO$^-$ or —SO$_2$O$^-$; and wherein n is an integer from 1 to 20.

11. A method of synthesizing a zwitterionic biopolymer compound, the method comprising:

functionalizing a biopolymer comprising a lignin with: one or more positively charged functional groups; one or more negatively charged functional groups; and one or more zwitterionic functional groups such that the biopolymer compound is substantially zwitterionic.

12. The method of claim 11, wherein the functionalizing comprises functionalizing the biopolymer with a zwitterionic functional group selected from the group consisting of sulfobetaine acrylates, sulfobetaine acrylamides, sulfobetaine vinyl compounds, sulfobetaine epoxides, sulfobetaine methacrylate, carboxybetaine acrylates, carboxybetaine acrylamides, carboxybetaine vinyl compounds, carboxybetaine epoxides, carboxybetaine methacrylate, and mixtures thereof.

13. The method of claim 11, wherein the functionalizing comprises functionalizing the biopolymer with a zwitterionic functional group selected from a cephalosporin-based antimicrobial functional group, cefepime, cephaloridine, and a combination thereof.

14. The method of claim 11, wherein the functionalizing comprises functionalizing the biopolymer with:

at least one positively charged chloroformate; and at least one negatively charged chloroformate.

15. The method of claim 14, further comprising preparing the at least one positively charged chloroformate by:

contacting a positively charged compound of formula: HO—(C$_{1-20}$)alkyl-Q$^\oplus$ with carbon monoxide, sulphur, 1,8-diazabicyclo[5.4.0]undec-7-ene, or a combination thereof followed by treatment with sulfuryl chloride to form a chloroformate of the formula: Cl—C(O)—O—(C$_{1-20}$)alkyl-Q$^\oplus$, wherein Q$^\oplus$ is a positively charged moiety selected from NR$^1$R$^2$R$^3$ wherein $R^1$, $R^2$, and $R^3$ are independently $C_{1-20}$ alkyl, $C_{6-20}$ aryl, $C_{3-20}$ cycloalkanes, $C_{1-20}$ alkyl acetamide of formula $C_nH_{(2n+1)}$—C(O)—N(CH$_2$)$_2$, $C_{1-20}$alkyloxybenzene, methoxy benzene, (2-ethoxy-ethoxy)-4-(1,1,3,3-tetramethyl-butyl)-benzene, and N-phenyl-acetamide; and wherein $R^1$, $R^2$, and $R^3$ may be joined together with the nitrogen to which they are attached to form a $C_{5-7}$ heterocycle.

16. The method of claim 15, wherein the contacting comprises contacting the positively charged compound of formula HO—(C$_{1-20}$)alkyl-Q$^\oplus$, wherein Q$^\oplus$ is selected from the group consisting of benzalkonium, benzethonium, methylbenzethonium, cetalkonium, cetylpyridinium, cetrimonium, cetrimide, dofanium, tetraethylammonium, didecyldimethylammonium, domiphen, and combinations thereof.

17. The method of claim 14, further comprising preparing the at least one negatively charged chloroformate by:

contacting a negatively charged compound of formula: HO—R$^4$—Z$^\ominus$ with carbon monoxide, sulphur, 1,8-diazabicyclo[5.4.0]undec-7-ene, or a combination thereof followed by treatment with sulfuryl chloride to form a chloroformate of the formula: Cl—C(O)—O—R$^4$—Z$^\ominus$, wherein $Z^\oplus$ is a negatively charged moiety selected from —SO$_3^\ominus$ and —COO$^\ominus$; and wherein $R^4$ is a bond, $C_{1-20}$ alkyl or arylene.

18. The method of claim 14, wherein the functionalizing comprises functionalizing lignin with the positively charged functional group 2-(trimethylammonium chloride) ethanol and the negatively charged functional group 3-sulphopropyl.

19. The method of claim 14, wherein the biopolymer is lignin and the method further comprises dissolving the lignin in dimethylsulfoxide, pyridine or a combination thereof prior to functionalizing the lignin with the at least one positively charged chloroformates and the at least one negatively charged chloroformates.

20. The method of claim 11, wherein functionalizing the biopolymer comprises functionalizing the biopolymer with the zwitterionic functional group of a formula: ($^\oplus$NR$^1$R$^2$R$^3$)—(CR$^5$R$^6$)$_n$—(R$^{7\ominus}$);

wherein each $R^1$, $R^2$, and $R^3$ is independently $C_{1-20}$ alkyl, $C_{6-20}$ aryl, $C_{3-20}$ cycloalkane, $C_{1-20}$ alkyl acetamide of formula $C_nH_{(2n+1)}$—C(O)—N(CH$_2$)$_2$, $C_{1-20}$ alkyloxybenzene, methoxy benzene, (2-ethoxy-ethoxy)-4-(1,1,3,3-tetramethyl-butyl)-benzene, N-phenyl-acetamide or an oligomer of ethylene glycol;

wherein any two of $R^1$, $R^2$, and $R^3$ may be joined together with the nitrogen to which they are attached to form a $C_{5-7}$ heterocycle;

wherein each $R^5$ and $R^6$ is independently H, OH, or $C_{1-20}$ alkyl;

wherein at least one $R^5$ or $R^6$ is selected from —OH, C—O—C(O)—NH$_2$ or —OC(O)OH;

wherein $R^7$ is —COO$^-$ or —SO$_2$O$^-$;

wherein n is an integer from 1 to 20.

21. A method of protecting a surface from the formation of a biofilm, the method comprising:

providing a zwitterionic biopolymer matrix comprising a lignin having one or more zwitterionic functional groups, one or more positively charged functional groups, and one or more negatively charged functional groups;

combining the zwitterionic biopolymer matrix with a base selected from paint, coating, varnish, stain, or a combination thereof;

coating the surface with the mixture; and allowing the mixture to cure, whereby the cured mixture will reduce the formation of a biofilm on the surface.

22. The method of claim 21, wherein coating the surface comprises coating the surface is selected from the hull of a ship, an automotive part, an automotive body panel, an amphibious vehicle part, an amphibious vehicle body panel, an aircraft part, an aircraft body panel, a turbine, a fan, an air conditioner, an air conditioner part, a refrigeration unit, a refrigeration unit part, a humidifier, a humidifier part, a dehumidifier, a dehumidifier part, a cooling tower, a cooling tower part, a water storage tank, a water storage tank part, a water storage container, a tanker, a hose, a hose fitting, a vent, ductwork, a pipe, a tube, a plumbing part, a plumbing tool, a swimming pool, swimming pool equipment, a ceramic tile, a glass window pane, a plastic window pane, hospital equipment, culinary equipment or a textile, a spa, a shower, a bathtub, a sink, a porcelain tile, a faucet, a shower curtain, a drain, a sewer, a kitchen counter, a kitchen cabinet, a food preparation area, a surface in a hospital setting, sports and recreation equipment, food processing and handling machinery, a business machine, a consumer appliance, a general household good, a transportation interior, construction supplies, a medical device, a pair of forceps, a clamp, an occluder, a retractor, a distractor, a scalpel, a lancet, a drill bit, a rasp, a trocar, a ligature, a dilator, a specula, a suction tip, a suction tube, a tyndaller, a drill, a dermatome, a scope, a probe, an endoscope, a tactile probe, a carrier, an applier, an ultrasound tissue disruptor, a cryotome, a laser cutting guide, a measurement device, a caliper, a stent, a catheter, a guide wire, a denture, a bridge, a crown, a pin, a rod, a screw, a plate, a prosthetic, a hip joint, a pacemaker, a cochlear implant and a drug eluting stent.

* * * * *

UNITED STATES PATENT AND TRADEMARK OFFICE
CERTIFICATE OF CORRECTION

PATENT NO. : 9,150,734 B2  
APPLICATION NO. : 13/522429  
DATED : October 6, 2015  
INVENTOR(S) : Brizius It is certified that error appears in the above-identified patent and that said Letters Patent is hereby corrected as shown below:

In the Specification

In Column 1, Lines 6-7, delete "under 35 U.S.C. §371" and insert -- under 35 U.S.C. § 371 --, therefor.

In Column 2, Line 51, delete "n-($R^{7\ominus}$). Each $R^1$, $R^2$, $R^3$" and insert -- n-(R7⊖). Each R1, R2, R3 --, therefor.

In Column 6, Line 19, delete "such as lignin Lignin" and insert -- such as lignin. Lignin --, therefor.

Signed and Sealed this
Twenty-ninth Day of March, 2016

Michelle K. Lee
*Director of the United States Patent and Trademark Office*